United States Patent
Boyd et al.

(10) Patent No.: US 7,304,142 B2
(45) Date of Patent: Dec. 4, 2007

(54) MAMMALIAN MDM2 BINDING PROTEINS

(75) Inventors: Mark Thomas Boyd, Handbridge (GB); Dale Stewart Haines, Wynnewood, PA (US); Nikolina Vlatkovic, Handbridge (GB)

(73) Assignee: Philadelphia, Health and Education Corporation, Philadelphia, PA (US)

( * ) Notice: Subject to any disclaimer, the term of this patent is extended or adjusted under 35 U.S.C. 154(b) by 0 days.

(21) Appl. No.: 11/650,159

(22) Filed: Jan. 5, 2007

(65) Prior Publication Data

US 2007/0129324 A1 Jun. 7, 2007

Related U.S. Application Data

(62) Division of application No. 10/312,954, filed as application No. PCT/US01/22053 on Jul. 12, 2001, now Pat. No. 7,166,712.

(60) Provisional application No. 60/230,894, filed on Sep. 5, 2000, provisional application No. 60/217,835, filed on Jul. 12, 2000.

(51) Int. Cl.
*C12N 15/12* (2006.01)
*C12N 15/70* (2006.01)
*C12N 15/79* (2006.01)
*C07K 14/435* (2006.01)

(52) U.S. Cl. ............... 530/358; 435/69.1; 435/252.3; 435/320.1; 536/23.1

(58) Field of Classification Search ............... None
See application file for complete search history.

(56) References Cited

U.S. PATENT DOCUMENTS

| | | | |
|---|---|---|---|
| 6,083,723 A * | 7/2000 | Tekamp-Olson | 435/69.4 |
| 6,204,253 B1 * | 3/2001 | Lu et al. | 514/44 |
| 6,265,165 B1 * | 7/2001 | Xu et al. | 435/6 |
| 6,372,490 B1 * | 4/2002 | Nandabalan et al. | 435/325 |
| 7,166,712 B2 * | 1/2007 | Boyd et al. | 536/23.1 |

OTHER PUBLICATIONS

VanDevanter et al., 1994, "Pure chromosome-specific PCR libraries from single sorted chromosomes", Proceedings of the NationalAcademy of Sciences, USA, vol. 91 No. 13, pp. 5858-5862.*

Boyd et al., 2000, "Assignment of MDM2 binding protein gene (MTBP) to human chromosome band 8q24 by in situ hybridization", Cytogenetics and Cell Genetics, vol. 90, Nos. 1-2, pp. 64-65.*

Marra et al., Oct. 10, 1999, NCBI genbank accession No. AI1430313, National Library of Medicine,.Bethesda MD.*

Juven-Gershon et al., The Mdm2 Oncoprotein Interacts with the Cell Fate Regulator Numb, Molecular and Cellular Biology 1998 18(7):3974-3982.*

Boyd et al., "A Novel Cellular Protein (MTBP) Binds to MDM2 and Induces a $G_1$ Arrest That Is Suppressed by MDM2", J. Biol. Chem. 2000 275(41):31883-31890.

Juven-Gershon et al., "The Mdm2 Oncoprotein Interacts with the Cell Fate Regulator Numb", Molecular and Cellular Biology 1998 18(7):3974-3982.

Sharp et al., "Stabilization of the MDM2 Oncoprotein by Interaction with the Structurally Related MDMX Protein", J. Biol. Chem. 1999 274(53):38189-38196.

Vlatkovic et al., "A Novel MDM2 Binding Protein (MTBP) Induces A G1 Arrest that is Suppressed by MDM2", British Journal of Cancer 2000 83(3a):P125.

* cited by examiner

*Primary Examiner*—Nashaat T. Nashed
*Assistant Examiner*—William W. Moore
(74) *Attorney, Agent, or Firm*—Licata & Tyrrell P.C.

(57) ABSTRACT

Isolated nucleic acid sequences encoding mammalian MDM2 binding protein and polypeptide sequences for the mammalian MDM2 binding protein are provided. Also provided are vectors containing these nucleic acid sequences, host cells which express these proteins and antibodies targeted to these proteins. In addition, methods and compositions for modulating the $G_1$ phase of the cell cycle via altering expression and/or activity of a mammalian MDM2 binding protein are provided.

2 Claims, No Drawings

SEQUENCE LISTING

<160> NUMBER OF SEQ ID NOS: 12

<210> SEQ ID NO 1
<211> LENGTH: 5768
<212> TYPE: DNA
<213> ORGANISM: Mus sp.

<400> SEQUENCE: 1

```
aatttcccac aataattggc gggaaaaccg acgtaggaca ttattttgca gccaacctga      60
gcggcaggaa accggaagtg cacgttgcgc gcggctcttt tgagacctaa cactgagtcc     120
gggcgcgaag aggatggatc ggtacttgct gctggtcacc tggagggaag ggaagtttcg     180
atccgtggcg ggtgggggaga tcgagcctgg cactgaggcg acatccctgg agagcaccga    240
caaacagccc gatttgaccg caaccaatat ttatcacctc ttgaagagaa gcatcagcga     300
ttcaatccat ccagatgaca gtacattccc tgcttgttca gtgggtggca cacctcattc    360
caggaagtgg ttctttgcgg tgcaagcaat atgcggattt taccagtttt gtagttctga     420
ttggcaagag atacattttg atgctgaaaa agataaaatc gaagatgttc ttcaagcaaa     480
tatagaagaa cgtcagagtg ctgttgagtg ttttgaagaa gatgacagta atagcaggga     540
atccttaccc ttggctgacg tatatgaaga atcagcagaa aatttgcatc agttatcaga     600
caagcttccc gctcctggta gagcaatgat agacataata ctgttgcctt ctgacaaaga     660
ccctcgtaag ctaaaagagt gcttgcccat tgtagggggcc ttgaaacatc tgaaggaatg     720
gcattcagca aaagttatca tagcaggaag ttactgtgag ataaattgtc agaaaattgc     780
tgaataccttt tcagctagtg ttgtgccttt agaagaattc agaaatgcca ttgatccgag     840
ggaagtgtgg cgggagaga ttcagatgcg ggaacgaaag tttggatttg aaattagttt     900
acctgaattt tgtttaaaag gagttacgcc tacgaatgtt agtgcgtata atttaaatac     960
ctgcttcctt gccaagaaga tagcatcttc taaggttttc cattattatg gtcctgcttt    1020
ggaatttgtg cagatgataa aactatcaga tcttccctcc tgttacatgt cggatatcga    1080
gtttgagtta gaggtgactg ggcactgcac gaggcagaat tccatgctgc tgttggaaca    1140
gatctcttcc ctgtgtggca aggttggtgc tctctttgtg ctgccgtgta ctgttagcaa    1200
tgtactcatc ccacctccca gccaactggc ctcaagaaag tggaaggaat acatggctaa    1260
gaagcccaag accatcagtg ttcccgatgt tgccgtgaag ggagagttttt ctggctatca    1320
tctcctgctg caaggtatgg gcaagagaaa atgcagagcc accctgctgc actcggccag    1380
ccagatcaat ggctcgtttg cactcagtgt cattcatggg aagatgaaaa caaaggcagg    1440
agaagccaga ccgagtttcc cctttgactt ctcgtcactc ccaaggtttt cggaggagca    1500
```

-continued

```
ggttttacag agagagaaac aattagccag cttcaagtt ttggctttga aagaatgcct     1560
gaaaagaaga aaggctgcaa accagcccga agccttttct gccgatgaac tcaaaagtct     1620
gttggcactc acgagggagc gcttcctagg tcactttgat gttctcccca ctgaagcagc     1680
tttagcacaa acagacaccg tgaaagctgc cggcgtggta aatgatgacg gtacagttga     1740
accttattct tcaagcctaa tggaaaccaa tcctctggaa tggccagaaa gacatgttct     1800
tcagaattta gaaacttctg aaaaagctaa acaaaaaatg agaactggct cattaccgcg     1860
ttcgtctgaa cagttgctgg gccataaaga gggtccccgg gactcactca cattactgga     1920
tgctaaggag ctgctgaagt atttcacctc ggatgggtta ccagtcggag atcttcagcc     1980
gttacacatt aacgggggg aaaagccttt tgttttgaca ccagagctta gtcctggaaa     2040
acttcaggtc ttaccttttg aaaaagcctc ggaatgccat taccacggga ttgaatattg     2100
cctggatgac caaaaagctt tagaaagaga tggggatttt tctgaacttc agtcgcgcct     2160
tattcgttac gagacgcaga ccacctgcac cagagacagt tttccagtcc caccgtgct     2220
gagccctctt ccatcccctg cagttctgtc agagcctcaa agtgtccccg aaggagaagc     2280
actgcaaggc gaactgagga ctgaagtttc tggattgaag cggagatcta aagacccag     2340
ctgcctgtac ccccagaaaa gacttacgag atcagaaagt tctgattgtt tgccttccca     2400
agcgagttgc aatagtaatc atcaccatca cacaggaaaa cccaggaagc ctcaggcaga     2460
gcgctgtgtg tcagggcttc ctctgcctgg ccgggaagct tccaaagata cctcaaagac     2520
cagttcagga caaaacgag cacacgaatc aaaatcatca aagcaaatga aggaatcacg     2580
gtcccagaaa cacacacgga tgctgaagga ggtggtaaaa gacaccttga agaggcacca     2640
catcacggag gcccatgaga gcttcacggc ctgcagccag agactcttcg acatctccaa     2700
aattcccac aataattggc gggaaaaccg acgtaggaca ttatttgca gccaacctga     2760
gcggcaggaa accggaagtg cacgttcgc gcggctcttt tgagacctaa cactgagtcc     2820
gggcgcgaag aggatggatc ggtacttgct gctggtcacc tggagggaag gaagtttcg     2880
atccgtggcg ggtgggaga tcgagcctgg cactgaggcg acatccctgg agagcaccga     2940
caaacagccc gatttgaccg caaccaatat ttatcacctc ttgaagagaa gcatcagcga     3000
ttcaatccat ccagatgaca gtacattccc tgcttgttca gtgggtggca cactcattc     3060
caggaagtgg ttctttgcgg tgcaagcaat atgcggattt taccagtttt gtagttctga     3120
ttggcaagag atacattttg atgctgaaaa agataaaatc gaagatgttc ttcaagcaaa     3180
tatagaagaa cgtcagagtg ctgttgagtg ttttgaagaa gatgacagta atagcaggga     3240
atccttaccc ttggctgacg tatatgaaga atcagcagaa aatttgcatc agttatcaga     3300
caagcttccc gctcctggta gagcaatgat agacataata ctgttgcctt ctgacaaaga     3360
ccctcgtaag ctaaaagagt gcttgcccat tgtaggggcc ttgaaacatc tgaaggaatg     3420
gcattcagca aaagttatca tagcaggaag ttactgtgag ataaattgtc agaaaattgc     3480
tgaataccct tcagctagtg ttgtgccttt agaagaattc agaaatgcca ttgatccgag     3540
ggaagtgtgg cggggagaga ttcagatgcg ggaacgaaag tttggatttg aaattagttt     3600
rcctgaattt tgtttaaaag gagttacgcc tacgaatgtt agtgcgtata atttaaatac     3660
ctgcttcctt gccaagaaga tagcatcttc taaggttttc cattattatg gtcctgcttt     3720
ggaatttgtg cagatgataa aactatcaga tcttccctcc tgttacatgt cggatatcga     3780
gtttgagtta gaggtgactg ggcactgcac gaggcagaat tccatgctgc tgttggaaca     3840
gatctcttcc ctgtgtggca aggttggtgc tctctttgtg ctgccgtgta ctgttagcaa     3900
```

-continued

| | |
|---|---|
| tgtactcatc ccacctccca gccaactggc ctcaagaaag tggaaggaat acatggctaa | 3960 |
| gaagcccaag accatcagtg ttcccgatgt tgccgtgaag ggagagtttt ctggctatca | 4020 |
| tctcctgctg caaggtatgg gcaagagaaa atgcagagcc accctgctgc actcggccag | 4080 |
| ccagatcaat ggctcgtttg cactcagtgt cattcatggg aagatgaaaa caaaggcagg | 4140 |
| agaagccaga ccgagtttcc cctttgactt ctcgtcactc ccaaggtttt cggaggagca | 4200 |
| ggttttacag agagagaaac aattagccag ctttcaagtt ttggctttga agaatgcct | 4260 |
| gaaaagaaga aaggctgcaa accagcccga agccttttct gccgatgaac tcaaaagtct | 4320 |
| gttggcactc acgagggagc gcttcctagg tcactttgat gttctcccca ctgaagcagc | 4380 |
| tttagcacaa acagacaccg tgaaagctgc cggcgtggta aatgatgacg gtacagttga | 4440 |
| accttattct tcaagcctaa tggaaaccaa tcctctggaa tggccagaaa gacatgttct | 4500 |
| tcagaattta gaaacttctg aaaaagctaa acaaaaaatg agaactggct cattaccgcg | 4560 |
| ttcgtctgaa cagttgctgg gccataaaga gggtccccgg gactcactca cattactgga | 4620 |
| tgctaaggag ctgctgaagt atttcacctc ggatgggtta ccagtcggag atcttcagcc | 4680 |
| gttacacatt caacgggggg aaaagccttt tgttttgaca ccagagctta gtcctggaaa | 4740 |
| acttcaggtc ttaccttttg aaaaagcctc ggaatgccat taccacggga ttgaatattg | 4800 |
| cctggatgac caaaaagctt tagaaagaga tgggggattt tctgaacttc agtcgcgcct | 4860 |
| tattcgttac gagacgcaga ccacctgcac cagagacagt tttccagtcc ccaccgtgct | 4920 |
| gagccctctt ccatcccctg cagttctgtc agagcctcaa agtgtcccg aaggagaagc | 4980 |
| actgcaaggc gaactgagga ctgaagtttc tggattgaag cggagatcta agacccccag | 5040 |
| ctgcctgtac ccccagaaaa gacttacgag atcagaaagt tctgattgtt tgccttccca | 5100 |
| agcgagttgc aatagtaatc atcaccatca cacagggaaa cccaggaagc ctcaggcaga | 5160 |
| gcgctgtgtg tcagggcttc ctctgcctgg ccgggaagct tccaaagata cctcaaagac | 5220 |
| cagttcagga caaaaacgag cacacgaatc aaaatcatca agcaaatga aggaatcacg | 5280 |
| gtcccagaaa cacacacgga tgctgaagga ggtggtaaaa gacaccttga agaggcacca | 5340 |
| catcacggag gcccatgaga gcttcacggc ctgcagccag agactcttcg acatctccaa | 5400 |
| gttctacctg aaggatctga aaacatcaag gggtctcttt gaagaaatga gaaaacagc | 5460 |
| caacaacaat gtggtgcagg tgatcgaatg ggtggtagaa aagatgagca agaaataagc | 5520 |
| tactgcaccc ccttcctta gagaactgta cacagcctgt aaactttccc caagagcag | 5580 |
| atgcctcatt tgtaaggagg gtccatggtg tcctgtatct atatagtttt gtgacactca | 5640 |
| gttattttca actaatgcac ttatttttac agttttacaa tatttaatc tatgaaattt | 5700 |
| ttatatattt taaatgtttt aactcttggt tatttaattg ttaaataaac agtaaggtaa | 5760 |
| atctcgag | 5768 |

<210> SEQ ID NO 2
<211> LENGTH: 914
<212> TYPE: PRT
<213> ORGANISM: Homo sapiens

<400> SEQUENCE: 2

Met Asp Arg Tyr Leu Leu Leu Val Ile Glu Trp Gly Glu Gly Lys Phe
 1               5                  10                  15

Pro Ser Ala Ala Ser Arg Glu Ala Glu His Gly Pro Glu Val Ser Ser
            20                  25                  30

```
Gly Glu Gly Thr Glu Asn Gln Pro Asp Phe Thr Ala Ala Asn Val Tyr
            35                  40                  45

His Leu Leu Lys Arg Ser Ile Ser Ala Ser Ile Asn Pro Glu Asp Ser
    50                  55                  60

Thr Phe Pro Ala Cys Ser Val Gly Gly Ile Pro Gly Ser Lys Lys Trp
65                  70                  75                  80

Phe Phe Ala Val Gln Ala Ile Tyr Gly Phe Tyr Gln Phe Cys Ser Ser
                85                  90                  95

Asp Trp Gln Glu Ile His Phe Asp Thr Glu Lys Asp Lys Ile Glu Asp
                100                 105                 110

Val Leu Gln Thr Asn Ile Glu Lys Cys Leu Gly Ala Val Glu Cys Phe
            115                 120                 125

Glu Glu Glu Asp Ser Asn Ser Arg Glu Ser Leu Ser Leu Ala Asp Leu
            130                 135                 140

Tyr Glu Glu Ala Ala Glu Asn Leu His Gln Leu Ser Asp Lys Leu Pro
145                 150                 155                 160

Ala Pro Gly Arg Ala Met Val Asp Ile Ile Leu Leu Leu Ser Asp Lys
                165                 170                 175

Asp Pro Pro Lys Leu Lys Asp Tyr Leu Pro Thr Val Gly Ala Leu Lys
                180                 185                 190

His Leu Arg Glu Trp Tyr Ser Ala Lys Ile Thr Ile Ala Gly Asn His
            195                 200                 205

Cys Glu Ile Asn Cys Gln Lys Ile Ala Glu Tyr Leu Ser Ala Asn Val
            210                 215                 220

Val Ser Leu Glu Asp Leu Arg Asn Val Ile Asp Ser Lys Glu Leu Trp
225                 230                 235                 240

Arg Gly Lys Ile Gln Ile Trp Glu Arg Lys Phe Gly Phe Glu Ile Ser
                245                 250                 255

Phe Pro Glu Phe Cys Leu Lys Gly Val Thr Leu Lys Asn Phe Ser Thr
                260                 265                 270

Ser Asn Leu Asn Thr Asp Phe Leu Ala Lys Lys Ile Ile Pro Ser Lys
            275                 280                 285

Asp Lys Asn Ile Leu Pro Lys Val Phe His Tyr Tyr Gly Pro Ala Leu
            290                 295                 300

Glu Phe Val Gln Met Ile Lys Leu Ser Asp Leu Pro Ser Cys Tyr Met
305                 310                 315                 320

Ser Asp Ile Glu Phe Glu Leu Gly Leu Thr Asn Ser Thr Lys Gln Asn
                325                 330                 335

Ser Val Leu Leu Leu Glu Gln Ile Ser Ser Leu Cys Ser Lys Val Gly
            340                 345                 350

Ala Leu Phe Val Leu Pro Cys Thr Ile Ser Asn Ile Leu Ile Pro Pro
            355                 360                 365

Pro Asn Gln Leu Ser Ser Arg Lys Trp Lys Glu Tyr Ile Ala Lys Lys
    370                 375                 380

Pro Lys Thr Ile Ser Val Pro Asp Val Glu Val Lys Gly Glu Cys Ser
385                 390                 395                 400

Ser Tyr Tyr Leu Leu Leu Gln Gly Asn Gly Asn Arg Arg Cys Lys Ala
                405                 410                 415

Thr Leu Ile His Ser Ala Asn Gln Ile Asn Gly Ser Phe Ala Leu Asn
            420                 425                 430

Leu Ile His Gly Lys Met Lys Thr Lys Thr Glu Glu Ala Lys Leu Ser
            435                 440                 445

Phe Pro Phe Asp Leu Leu Ser Leu Pro His Phe Ser Gly Glu Gln Ile
```

```
            450                 455                 460
Val Gln Arg Glu Lys Gln Leu Ala Asn Val Gln Val Leu Ala Leu Glu
465                 470                 475                 480

Glu Cys Leu Lys Arg Arg Lys Leu Ala Lys Gln Pro Glu Thr Val Ser
                485                 490                 495

Val Ala Glu Leu Lys Ser Leu Leu Val Leu Thr Arg Lys His Phe Leu
            500                 505                 510

Asp Tyr Phe Asp Ala Val Ile Pro Lys Met Ile Leu Arg Lys Met Asp
            515                 520                 525

Lys Ile Lys Thr Phe Asn Ile Leu Asn Asp Phe Ser Pro Val Glu Pro
530                 535                 540

Asn Ser Ser Leu Met Glu Thr Asn Pro Leu Glu Trp Pro Glu Arg
545                 550                 555                 560

His Val Leu Gln Asn Leu Glu Thr Phe Glu Lys Thr Lys Gln Lys Met
                565                 570                 575

Arg Thr Gly Ser Leu Pro His Ser Ser Glu Gln Leu Leu Gly His Lys
                580                 585                 590

Glu Gly Pro Arg Asp Ser Ile Thr Leu Leu Asp Ala Lys Glu Leu Leu
            595                 600                 605

Lys Tyr Phe Thr Ser Asp Gly Leu Pro Ile Gly Asp Leu Gln Pro Leu
            610                 615                 620

Pro Ile Gln Lys Gly Glu Lys Thr Phe Val Leu Thr Pro Glu Leu Ser
625                 630                 635                 640

Pro Gly Lys Leu Gln Val Leu Pro Phe Glu Lys Ala Ser Val Cys His
                645                 650                 655

Tyr His Gly Ile Glu Tyr Cys Leu Asp Asp Arg Lys Ala Leu Glu Arg
                660                 665                 670

Asp Gly Gly Phe Ser Glu Leu Gln Ser Arg Leu Ile Arg Tyr Glu Thr
            675                 680                 685

Gln Thr Thr Cys Thr Arg Glu Ser Phe Pro Val Pro Thr Val Leu Ser
            690                 695                 700

Pro Leu Pro Ser Pro Val Val Ser Ser Asp Pro Gly Ser Val Pro Asp
705                 710                 715                 720

Gly Glu Val Leu Gln Asn Glu Leu Arg Thr Glu Val Ser Arg Leu Lys
                725                 730                 735

Arg Arg Ser Lys Asp Leu Asn Cys Leu Tyr Pro Arg Lys Arg Leu Val
                740                 745                 750

Lys Ser Glu Ser Ser Glu Ser Leu Leu Ser Gln Thr Thr Gly Asn Ser
                755                 760                 765

Asn His Tyr His His His Val Thr Ser Arg Lys Pro Gln Thr Glu Arg
770                 775                 780

Ser Leu Pro Val Thr Cys Pro Leu Val Pro Ile Pro Ser Cys Glu Thr
785                 790                 795                 800

Pro Lys Leu Ala Thr Lys Thr Ser Ser Gly Gln Lys Ser Met His Glu
                805                 810                 815

Ser Lys Thr Ser Arg Gln Ile Lys Glu Ser Arg Ser Gln Lys His Thr
                820                 825                 830

Arg Ile Leu Lys Glu Val Val Thr Glu Thr Leu Lys Lys His Ser Ile
                835                 840                 845

Thr Glu Thr His Glu Cys Phe Thr Ala Cys Ser Gln Arg Leu Phe Glu
            850                 855                 860

Ile Ser Lys Phe Tyr Leu Lys Asp Leu Lys Thr Ser Arg Gly Leu Phe
865                 870                 875                 880
```

Glu Glu Met Lys Lys Thr Ala Asn Asn Asn Ala Val Gln Val Lys Lys
            885                 890                 895

Leu Phe Pro Arg Asn Tyr Ile Gln Leu Asn Trp Tyr Phe Ile Ser Gly
        900                 905                 910

Leu Leu

<210> SEQ ID NO 3
<211> LENGTH: 2975
<212> TYPE: DNA
<213> ORGANISM: Homo sapiens

<400> SEQUENCE: 3

```
ggatgtggaa gccgagacct aaagttgggg ggtgatctct gaggagatgg atcggtacct    60
gctgctggtg atctgggggg aaggaaaatt cccgtcggcg gccagtaggg aggcagaaca   120
tgggccagag gtgtcgtcgg gtgagggtac tgagaatcag ccggacttca cagcagcaaa   180
tgtttatcac ctcttgaaaa gaagcattag tgcttcaatt aatccagaag atagtacttt   240
ccctgcctgt tcagtgggag gtatacctgg ttccaagaag tggttctttg cagtgcaggc   300
aatatatgga ttttatcagt tttgtagttc tgattggcaa gagatacatt ttgatacaga   360
aaaagataaa attgaagatg ttcttcaaac gaatatcgaa aaatgtttgg gtgctgttga   420
gtgttttgaa gaagaagaca gtaatagcag ggaatcatta tccttggctg atctctatga   480
agaagctgca gaaaatttgc atcagctgtc agacaagctt cctgctcctg gtagagcaat   540
ggtagatata atactgttgc tttctgacaa agatcctcct aaattgaaag actatttacc   600
tactgtagga gcattaaaac atttgagaga atggtattca gcaaagatca ctatagcagg   660
aaatcattgt gaaataaact gtcagaaaat tgcagaatac ctttctgcta atgttgtatc   720
tttagaagat ctcagaaatg ttattgactc aaaggaatta tggaggggga aaatacagat   780
atgggaaaga agtttggat ttgaaattag ctttcctgaa ttttgtttaa agggagtcac   840
acttaagaat tttagtactt ctaatttaaa tactgacttc cttgccaaaa agatcatacc   900
atcaaaggat aagaatattt tgccaaaggt ttttccattat tatggccctg ctttagaatt   960
tgtgcagatg ataaaattat cagatctacc ctcctgctat atgtcggata ttgaatttga  1020
gttaggattg acaaacagta ccaaacagaa ttctgtgttg ctgttggagc agatttcttc  1080
tctgtgtagc aaggttggtg ctcttttttgt attgccatgt accattagta acatactgat  1140
tccacctccc aaccaactca gttcaagaaa atggaaggaa tatatagcta aaaagcctaa  1200
aacaatcagt gttccagatg ttgaagtgaa aggagagtgt tctagctatt atctcttgtt  1260
acaaggtaat ggcaatagaa gatgtaaagc cacattgatt cactcagcca accagatcaa  1320
tggctcattt gcactcaatt taattcatgg aaagatgaaa acaaagacag aagaagccaa  1380
attgagtttt ccttttgact tattatcact tccacatttt tctggggagc agattgtaca  1440
gagagagaaa cagttagcta atgttcaagt tttagctttg gaagaatgcc taaaaagacg  1500
aaagttggca agcagcctg aaacagtttc tgttgctgaa ctcaaaagtc tgttagtact  1560
cacaaggaaa cacttttttag attattttga tgctgtgatt cctaaaatga ttctaagaaa  1620
gatggacaaa attaaaacct tcaatatatt aaatgatttt agtccagtgg aacctaattc  1680
ctcaagtcta atggaaacca atcctctgga atggccagaa aggcatgttc ttcaaaattt  1740
ggaaactttt gaaaaaacta acaaaaaat gagaactggt tcattacctc attcatctga  1800
acagttgctg ggccacaaag agggtcctcg ggactcaatc acattgttgg atgctaaaga  1860
```

-continued

```
attgctgaag tactttacct cagatggatt acccattgga gatcttcaac ctttaccgat    1920
tcaaaggggg gaaagacttt tgttttgac accagaactt agtcctggga aacttcaggt     1980
cttacctttt gagaaagcct cagtatgtca ttatcatgga attgaatatt gcttggatga    2040
ccgaaaagct ttggaaagag atggaggatt ttctgaactt cagtctcgtc ttattcgtta    2100
tgaaactcaa actacctgca ccagagaaag ttttccagta cctactgtgt tgagccctct    2160
tccatctcct gtagtttcgt cagatcctgg aagtgtccct gacggagaag ttttacaaaa    2220
tgaacttcga actgaagtat cccgattgaa acggagatct aaagatctga attgcccttta   2280 tcccagaaaa agacttgtga aatctgaaag ttcagagtcc cttctttctc agacaactgg    2340
taatagtaat cactatcatc atcatgtgac atccagaaag ccacaaacag agcggtcctt    2400
accagtgact tgtccattgg ttccaattcc tagctgtgaa actccaaaac ttgctacaaa    2460
gaccagttca ggtcaaaaaa gtatgcatga atcaaaaaca tcaaggcaaa ttaaggaatc    2520
aagatcacag aaacacacac ggatactgaa agaagtagtt actgaaaccc tgaagaaaca    2580
cagtattacc gagactcatg aatgtttcac tgcatgcagc cagcgtctct ttgaaatctc    2640
taagttctat ctaaaggatc ttaaaacttc aaggggtcta tttgaagaaa tgaagaaaac    2700
agcaaacaac aatgctgtac aggtaaagaa attattccca agaaactata ttcaattaaa    2760 ttggtattt atttcagggt tgctctgatg ccattatata tgcagcagta atcagttact     2820 ggtcttttc aactctgtcc ctatgaaaac tctttaagaa acttcatagg cttatttagg     2880
ctgagtattt catagtattt agtagattgc tctgtcagca aaagagtttc taaagtgaca    2940
ctaagaaagc aaaaaaaaaa aaaaaaaaaa aaaaa                                2975
```

```
<210> SEQ ID NO 4
<211> LENGTH: 418
<212> TYPE: PRT
<213> ORGANISM: Mus sp.
<220> FEATURE:
<221> NAME/KEY: unsure
<222> LOCATION: (418)
<223> OTHER INFORMATION: X=any amino acid

<400> SEQUENCE: 4

Arg Arg Lys Ala Ala Asn Gln Pro Glu Ala Phe Ser Ala Asp Glu Leu
  1               5                  10                  15

Lys Ser Leu Leu Ala Leu Thr Arg Glu Arg Phe Leu Gly His Phe Asp
                 20                  25                  30

Val Leu Pro Thr Glu Ala Ala Leu Ala Gln Thr Asp Thr Val Lys Ala
             35                  40                  45

Ala Gly Val Val Asn Asp Asp Gly Thr Val Glu Pro Tyr Ser Ser Ser
         50                  55                  60

Leu Met Glu Thr Asn Pro Leu Glu Trp Pro Glu Arg His Val Leu Gln
 65                  70                  75                  80

Asn Leu Glu Thr Ser Glu Lys Ala Lys Gln Lys Met Arg Thr Gly Ser
                 85                  90                  95

Leu Pro Arg Ser Ser Glu Gln Leu Leu Gly His Lys Glu Gly Pro Arg
                100                 105                 110

Asp Ser Leu Thr Leu Leu Asp Ala Lys Glu Leu Leu Lys Tyr Phe Thr
            115                 120                 125

Ser Asp Gly Leu Pro Val Gly Asp Leu Gln Pro Leu His Ile Gln Arg
        130                 135                 140

Gly Glu Lys Pro Phe Val Leu Thr Pro Glu Leu Ser Pro Gly Lys Leu
145                 150                 155                 160
```

```
Gln Val Leu Pro Phe Glu Lys Ala Ser Glu Cys His Tyr His Gly Ile
                165                 170                 175
Glu Tyr Cys Leu Asp Asp Gln Lys Ala Leu Glu Arg Asp Gly Gly Phe
            180                 185                 190
Ser Glu Leu Gln Ser Arg Leu Ile Arg Tyr Glu Thr Gln Thr Thr Cys
        195                 200                 205
Thr Arg Asp Ser Phe Pro Val Pro Thr Val Leu Ser Pro Leu Pro Ser
    210                 215                 220
Pro Ala Val Leu Ser Glu Pro Gln Ser Val Pro Glu Gly Ala Leu
225                 230                 235                 240
Gln Gly Glu Leu Arg Thr Glu Val Ser Gly Leu Lys Arg Ser Lys
                245                 250                 255
Asp Pro Ser Cys Leu Tyr Pro Gln Lys Arg Leu Thr Arg Ser Glu Ser
            260                 265                 270
Ser Asp Cys Leu Pro Ser Gln Ala Ser Cys Asn Ser Asn His His His
        275                 280                 285
His Thr Gly Lys Pro Arg Lys Pro Gln Ala Glu Arg Cys Val Ser Gly
    290                 295                 300
Leu Pro Leu Pro Gly Arg Glu Ala Ser Lys Asp Thr Ser Lys Thr Ser
305                 310                 315                 320
Ser Gly Gln Lys Arg Ala His Glu Ser Lys Ser Ser Lys Gln Met Lys
                325                 330                 335
Glu Ser Arg Ser Gln Lys His Thr Arg Met Leu Lys Glu Val Val Lys
            340                 345                 350
Asp Thr Leu Lys Arg His His Ile Thr Glu Ala His Glu Ser Phe Thr
        355                 360                 365
Ala Cys Ser Gln Arg Leu Phe Asp Ile Ser Lys Phe Tyr Leu Lys Asp
    370                 375                 380
Leu Lys Thr Ser Arg Gly Leu Phe Glu Glu Met Lys Lys Thr Ala Asn
385                 390                 395                 400
Asn Asn Val Val Gln Val Ile Glu Trp Val Val Glu Lys Met Ser Lys
                405                 410                 415
Lys Xaa

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic

<400> SEQUENCE: 5
gagagactgc aggagaacac agatgagcta cctgg                             35

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic

<400> SEQUENCE: 6
gagagaaagc tgtcagctag ttgaagtaac ttagca                            36

<210> SEQ ID NO 7
<211> LENGTH: 24
<212> TYPE: DNA
```

```
<213> ORGANISM: Artificial Sequence
<220> FEATURE:
<223> OTHER INFORMATION: Description of Artificial Sequence: Synthetic

<400> SEQUENCE: 7
tgaagaataa ggttcaactg tacc                                          24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic

<400> SEQUENCE: 8
cagctttcac ggtgtctgtt tg                                            22

<210> SEQ ID NO 9
<211> LENGTH: 44
<212> TYPE: DNA
<213> ORGANISM: Artificial Sequence
<220> FEATURE:
<223> OTHER INFORMATION: Description of Artificial Sequence: Synthetic

<400> SEQUENCE: 9
gagagagcgg ccgcggcgcg aagaggatgg atcggtactt gctg                    44

<210> SEQ ID NO 10
<211> LENGTH: 75
<212> TYPE: DNA
<213> ORGANISM: Artificial Sequence
<220> FEATURE:
<223> OTHER INFORMATION: Description of Artificial Sequence: Synthetic

<400> SEQUENCE: 10
gagagagcgg ccgcctacag ggaggcgtaa tcgggcacat cgtagggta tttcttgctc    60 atcttttcta ccacc                                                    75

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic

<400> SEQUENCE: 11
gagagagata tcgccaattt taatcaaagt gggaatatt                          39

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic

<400> SEQUENCE: 12
gagagagcgg ccgctttcag tatctacgat tcatagatct c                       41
```

MAMMALIAN MDM2 BINDING PROTEINS

INTRODUCTION

This patent application is a divisional of U.S. patent application Ser. No. 10/312,954, filed Jun. 10, 2003, now U.S. Pat. No. 7,166,712, which is the U.S. National Phase of PCT Application Ser. No. PCT/US2001/22053, filed Jul. 12, 2001, which claims the benefit of priority from U.S. Provisional Application Ser. No. 60/230,894 filed Sep. 5, 2000, and U.S. Provisional Application Ser. No. 60/217,835 filed Jul. 12, 2000.

This invention was supported in part by funds from the U.S. government (NIH Grant No. CA70165) and the U.S. government may therefore have certain rights in the invention.

FIELD OF THE INVENTION

The present invention relates to the identification of mammalian genes, in particular a mouse and human gene, which encode a protein, referred to herein as MDM2 binding protein or MTBP, which is involved in the MDM2 growth regulatory pathway in cells. Specifically, it has been found that overexpression of MTBP can induce an arrest in the $G_1$ phase of the cell cycle. Further, it has been found that overexpression of MDM2 can block the arresting effects of MTBP in the $G_1$ phase of the cell cycle and that MDM2 can induce increased turnover of MTBP. Thus, it is believed that MTBP may have tumor suppressive activity. Accordingly, provided in the present invention are isolated nucleic acid sequences encoding MTBP, isolated polypeptide sequences for mammalian MTBP, vectors and host cells for expression of this cellular growth regulating protein and antibodies which target this cellular growth regulating protein.

Also provided in the present invention are methods and compositions for modulating the $G_1$ phase of the cell cycle via altering expression levels and/or activity of MTBP.

BACKGROUND OF THE INVENTION

In tumors, loss of function of either p53 itself (Hollstein et al. Nucleic Acids Res. 1996 24:141-146; Nigro et al. Nature 1989 342:705-708), or of the p53 dependent pathway that activates $G_1$ arrest, is one of the major and most frequent molecular events (reviewed in Sherr, C. J. Genes Dev. 1998 12:2984-2991). p53 function may be compromised directly, via genetic mutation and/or deletion of the p53 gene (Baker et al. Science 1989 244:217-221) and indirectly by changes in the regulation or level of the MDM2 protein (Oliner et al. Nature 1992 358:80-83). The MDM2 gene, itself a transcriptional target of p53 (Barak et al. EMBO J 1993 12:461-468; Juven et al. Oncogene 1993 8:3411-3416; and Wu et al. Genes Dev. 1993 7:1126-1132), encodes a protein, MDM2, that is a critical negative regulator of p53 function (Finlay, C. A. Mol. Cell. Biol. 1993 13:301-306; Momand et al. Cell 1992 69:1237-1245). MDM2 was originally discovered as an oncogene that was amplified on mouse double minute chromosomes (Cahilly-Snyder et al. Cell Mol. Genet. 1987 13:235-244). MDM2 was later found to be amplified and overexpressed in a variety of human cancers (Ladanyi et al. Cancer Res. 1993 1:16-18; Reifenberger et al. Cancer Res. 1993 53:2736-2739). MDM2 binds to the transcriptional activation domain of p53 and thus inhibits this function of p53 (Chen et al. Mol. Cell Biol. 1993 13:4107-4114; Oliner et al. Nature 1993 362:857-860). Moreover, MDM2 binding to p53 regulates the stability of the p53 protein such that p53 is ubiquitinated and is then degraded by the proteasome (Haupt et al. EMBO J. 1996 15:1596-1606; Kubbutat et al. Nature 1997 387:299-303). This, together with the observed effect upon p53 function, has led to a model in which an autoregulatory loop connects MDM2 and p53 (Barak et al. EMBO J 1993 12:461-468; Wu et al. Genes Dev. 1993 7:1126-1132).

MDM2 inhibits both p53 mediated $G_1$ arrest and apoptosis (Chen et al. Mol. Cell. Biol. 1996 16:2445-2452; Haupt et al. EMBO J 1996 15:1596-1606). p53 induces $G_1$ arrest by promoting transcriptional upregulation of the CDK inhibitor p21$^{waf1/cip1}$ (Waldmann et al. Cancer Res. 1995 55:5187-5190). Therefore, it is likely that MDM2 prevents p53 from inducing $G_1$ arrest by inhibiting p53 dependent transcriptional activation. MDM2 can prevent p53-mediated apoptosis, and this has been shown to be dependent upon the ability of MDM2 to inhibit transcriptional repression by p53 (Hsieh et al. Mol. Cell 1999 3:81-93). Moreover, a previously identified interaction with RB (Xiao et al. Nature 1995 375:694-698) was shown to be able to regulate this effect. By binding to MDM2, RB forms a stable ternary complex with p53 and this prevents the MDM2 promoted degradation of p53. The ternary complex can promote p53 dependent apoptosis but not p53 mediated transactivation.

The autoregulatory relationship between p53 and MDM2 suggests that MDM2 overexpression may be oncogenic because of the resulting inactivation of p53 (Wu et al. Genes Dev. 1993 7:1126-1132). This conclusion is supported by studies of human tumors which show that in the majority of cases either p53 is mutated/deleted or MDM2 is overexpressed (Leach et al. Cancer Res. 1993 53:2231-2234). Studies of allelic knockouts of these genes in mice further support the ability to negatively regulate p53 being a primary function of MDM2. Mice that possess a homozygous deletion of MDM2 die at around day 5 of embryogenesis whereas, mice that possess homozygous deletion of both MDM2 and p53 are viable and develop normally (Jones et al. Nature 1995 378:206-208; Montes de Oca Luna et al. Nature 1995 378:203-206). No differences have been detected between these p53 −/− and p53 −/−, MDM2 −/− mice in terms of the rate or spectrum of tumors developed (Jones et al. Proc. Natl Acad. Sci. USA 1996 93:14106-14111). Also, no differences could be detected between the embryonic fibroblasts derived from these animals in terms of their growth or cell cycle characteristics.

Collectively, these observations suggest that the primary function of MDM2 may be to regulate p53 activity and perhaps, during normal development, this is indeed the case. However, the situation appears to be different when MDM2 is expressed at abnormally high levels. Experiments in which MDM2 was overexpressed in NIH3T3 cells have shown that naturally occurring splice variants of MDM2 that lack the ability to bind to p53 are still able to transform these cells (Sigala et al. Nat. Med. 1996 2:912-917). Further support for the suggestion that MDM2 has p53 independent effects is derived from studies of transgenic mice. Mice transgenic for an MDM2 gene expressed from a β-lactoglobulin promoter, exhibited abnormal mammary development, with cells becoming polyploid together with a multinucleate morphology, suggestive of DNA synthesis in the absence of mitosis (Lundgren et al. Genes Dev. 1997 11:714-725). The same results were obtained in both p53 wild type animals and in animals with homozygous deletion of p53. In addition, recent studies using a different transgenic system with multiple copies of the whole MDM2 gene being used to generate mice that overexpress MDM2 from the MDM2 promoter, have shown that these animals develop a different spectrum of tumors c.f. p53 null mice (Jones et al. Proc. Natl Acad. Sci. USA 1998 95:15608-15612). The same effect of MDM2 overexpression was observed regardless of the p53 status of these animals. Finally, in support of the existence of p53 independent effects of MDM2 upon overexpression, it has recently been shown that MDM2 has the ability to abrogate the growth inhibitory activities of Transforming Growth Factor-Beta1 (TGFβ1). This effect was p53 independent in cells in culture (Sun et al. Science 1998 282: 2270-2272). Taken together, these results all suggest that overexpression of MDM2 acts not only upon p53 but also on additional pathways.

Using a yeast two hybrid screen a novel gene encoding a protein referred to herein as MTBP for MDM2 (Two) Binding Protein has now been identified. MTBP is demonstrated herein to be capable of negatively regulating growth by inducing $G_1$ arrest in a p53 independent manner. Further, this negative regulation of growth can be suppressed by MDM2.

SUMMARY OF THE INVENTION

An object of the present invention is to provide isolated nucleic acid sequences encoding a mammalian MDM2 binding protein.

Another object of the present invention is to provide vectors and host cells expressing vectors which comprise nucleic acid sequences encoding a mammalian MDM2 binding protein.

Another object of the present invention is to provide isolated polypeptide sequences of a mammalian MDM2 binding protein.

Another object of the present invention is to provide antibodies which target a mammalian MDM2 binding protein or a fragment thereof.

Yet another object of the present invention is to provide methods and compositions for modulating the $G_1$ phase of the cell cycle via altering expression of a mammalian MDM2 binding protein or levels and/or activity of a mammalian MDM2 binding protein. Examples of compositions capable of modulating expression of a mammalian MDM2 binding protein or levels or activity of this protein include, but are not limited to, antisense agents targeted to a gene encoding a mammalian MDM2 binding protein, ribozymes targeted to a gene encoding a mammalian MDM2 binding protein, peptide mimics of a mammalian MDM2 binding protein, antibodies targeted to a mammalian MDM2 binding protein and modulators of MDM2 expression.

DETAILED DESCRIPTION OF THE INVENTION

The MDM2 protein, through its interaction with p53 plays an important role in the regulation of the $G_1$ checkpoint of the cell cycle. In addition to binding to and inhibiting the transcriptional activation function of the p53 protein, MDM2 binds, inter alia, to RB, and the E2F-1/DP-1 complex and in so doing is believed to promote progression of cells into S-phase. Mice transgenic for MDM2 possess cells that have cell cycle regulation defects and develop an altered tumor profile independent of their p53 status. MDM2 also blocks the growth inhibitory effects of TGF-PI in a p53 independent manner.

The present invention relates to a novel growth regulatory molecule which is also the target of MDM2 mediated inhibition. Using a yeast two-hybrid screen, a gene that encodes a cellular protein, referred to herein as MDM2 binding protein (MTBP), that binds to MDM2 has now been identified. As demonstrated herein, MTBP induces $G_1$ arrest. As also demonstrated herein, MTBP induction can in turn be blocked by MDM2. These results indicate MTBP to be involved in a p53-independent growth control pathway regulated, at least in part, by MDM2. It is believed that the protein of the present invention, MTBP provides an additional link between MDM2 function and regulation of the $G_1$ cell cycle checkpoint. Thus, like a number of tumor suppressor proteins such as p53, E2F-1, RB and p19$^{Arf}$ which interact with MDM2, MTBP when expressed at high levels can induce growth arrest in vitro. It is therefore believed that the MTBP protein of the present invention may also be a tumor suppressor protein.

The MTBP gene and protein of the present invention was first identified in experiments wherein a full length CDNA for murine MDM2 was subcloned into a GAL4 DNA binding domain (GAL4-DBD) yeast expression construct and used to screen a murine T cell lymphoma cDNA library. A carboxy terminal cDNA from a novel gene fused to the activation domain of GAL4 (GAL-4-AD-3'MTBP) was found to interact with GAL4-DBD-MDM2 but not with GAL4-DBD. This interaction was confirmed in a different system wherein the in vitro translated cDNA from the yeast two hybrid screen (pBBV-3'MTBP) was mixed with recombinant His$_6$-tagged MDM2. pBBV-3'MTBP encodes a peptide that can bind in vitro to MDM2. Sequence analysis of this cDNA demonstrated that it is a novel sequence that encodes a predicted peptide of 380 amino acids. Northern analysis demonstrated that the carboxy terminal cDNA hybridized to a mRNA of approximately 3 kb. The rest of the cDNA for this gene was cloned using a RACE-based strategy. Analysis of 5' RACE products from mRNA obtained from a murine B cell line showed several clones possessing an authentic 5' end; the clones were identical and terminated upstream of a single long open reading frame that was in frame with the clone identified in the yeast two hybrid screen. The sequence of this murine clone has been deposited in the Genbank data base (AJ278508) and is depicted herein as SEQ ID NO:1. This cDNA encodes a protein (depicted in SEQ ID NO:4) with a predicted Mw of 104 kD, and this gene is referred to herein as MDM2 (Two) binding protein or MTBP. We have also referred to this gene as p104.

A cDNA for human MTBP has also been isolated and sequenced. The sequence of this cDNA and the polypeptide encoded thereby are depicted in SEQ ID NO:3 and 2, respectively.

Database analysis identified two yeast genes, BOI1 and BOI2, whose protein products possessed significant homology to murine MTBP,(Bender et al. J. Cell Biol. 1996 133:879-894; Matsui et al. J. Cell Biol. 133:865-878). The two proteins encoded by the genes, Boi1p and Boi2p, exhibit an overall amino acid identity of 38% which is concentrated into four regions (I-IV) that possess identities of 71%, 65%, 78% and 69%, respectively. Both Boi1p and Boi2p inhibit growth in yeast when expressed at high levels. More specifically, these yeast proteins are part of a pathway that is required for maintenance of cell polarity which is necessary for bud formation. This pathway is regulated by Cdc42p, a member of the rho family of GTPases together with an associated GTP-GDP exchange factor Cdc24p (reviewed in Cabib et al. Annu. Rev. Biochem. 1998 67:307-333).

The homology between Boi1p, Boi2p and MTBP is 21.2% and 21% amino acid identity in alignments of 401 and 400 amino acids, respectively, and is entirely contained within the carboxy terminal regions of all three proteins. Interestingly, the growth inhibitory function of Boi2p is entirely contained within the carboxy terminal moiety of the protein. Thus, it is believed that MTBP may also play a role in the regulation of a Cdc42p dependent pathway.

Domain three of Boi2p is a proline rich region that is essential for binding to the second src homology region 3 (SH3-2) of Bem1p. The corresponding region of MTBP is also proline rich. Given that many SH3 binding proteins use a region that is rich in proline residues for binding (Grossman et al. Mol. Cell 1998 2:405-415), it is believed that the homologous region of MTBP may also bind to SH3 domains.

Apart from ESTs, no other substantial homologies to MTBP were identified.

Numerous sequence motifs were identified within MTBP. In particular, six potential nuclear localization signals were detected (both mono- and bi-partite), which are compatible with a nuclear localization for this protein.

The full length cDNA for murine MTBP was used to examine the pattern of expression of this gene by northern blot. MTBP is expressed in a variety of normal tissues with the highest levels of expression being in the thymus, testis and ovary and low or almost undetectable expression in peripheral blood lymphocytes. Thymus, testis and ovary are sites of high levels of cell proliferation and differentiation and moreover are the same tissues that exhibit the highest levels of expression of MDM2 (Fakharzadeh et al. EMBO J 1991 10:1565-1569). MTBP was also detected in pancreas, heart, liver, skeletal muscle, liver and relatively low expression was detected in brain.

The cDNA corresponding to amino acids 515 to 894 of MTBP was initially identified via its interaction with MDM2. To test whether the interaction detected between this carboxy terminal region of MTBP and MDM2 also occurred between the full length form of the protein, an in vitro binding assay was performed using recombinant $His_6$-MDM2 and in vitro translated MTBP. Both this fragment and the full length protein bound to MDM2 in an in vitro assay. This indicates that the interaction of MTBP with MDM2 is likely to be direct. Further confirmation of the interaction between these two proteins came from analysis of mammalian cells transfected with MDM2 and a carboxy-terminal hemagglutinin (HA) tagged form of MTBP. Further, immunoprecipitation with either an anti HA MAb or an anti MDM2 MAb followed by western blot analysis, demonstrated that the two proteins could be co-precipitated. These results indicate that the newly identified protein of the present invention, MTBP, binds specifically to MDM2 under these conditions.

The MDM2 protein has a number of highly conserved regions and the function of these is not fully understood (reviewed in Freedman et al. Cell Mol. Life Sci. 1999 55:96-107). The region of MDM2 that binds to MTBP was determined using a series of carboxy terminal deletion mutants of GAL4-DBD-MDM2. The ability of the mutants to interact in yeast with GAL4-AD-MTBP was assessed. An interaction was detected with all mutants containing the amino terminal 304 amino acids of MDM2 but not with shorter mutants. A p53 containing construct, GAL4-AD-p53, was also demonstrated to interact with these mutants as well as mutants 1-199 and 1-166, thus indicating that the failure of MTBP to bind to these mutants of MDM2 does not merely reflect lower expression or other conformational problems. The ability of in vitro translated full length MTBP and carboxy terminal MTBP (pBBV-3'MTBP) to bind to both full length MDM2 and to a mutant that lacks the first 166 amino acids (Δ166) was also examined. Δ166 does not bind to p53. However, it does bind to both full length MTBP and to pBBV-3'MTBP. Thus, taken together, these results indicate that a region of MDM2 bounded by amino acids 167 to 304 is sufficient to bind to MTBP. This region of MDM2 contains a nuclear localization signal, a region identified as a nuclear export signal and an acidic region. Results in both yeast and in vitro suggest that the carboxy terminal region of MTBP (amino acids 515-894) is sufficient for binding to MDM2. Thus, it is believed that MDM2 binds to the carboxy terminal 380 amino acids of MTBP and that the region of MDM2 from amino acid 167 to 304 is sufficient for the binding interaction to occur. This region of MDM2 overlaps with the MDM2 binding sites for p300, TFIIE, RB and $p19^{arf}$(Hsieh et al. Mol. Cell 1999 3:81-93; Xiao et al. Nature 1995 375:694-698; Grossman et al. Mol. Cell 1998 2:405-415; Pomerantz et al. Cell 1998 92:713-723; Zhang et al. Cell 1998 92:725-734; and Thut et al. Genes Dev. 1997 11:1974-1986). For example, the p300 binding region of MDM2 lies between amino acids 102 and 222. p300 binding to MDM2 has been shown to be necessary for MDM2 mediated degradation of p53. The region responsible for interaction of MDM2 with the 34 kD subunit of TFIIE lies between MDM2 amino acids 50-222. This interaction has been implicated in the ability of MDM2 to function as a transcriptional repressor. The region of MDM2 responsible for binding to RB, amino acids 272 to 320, also overlaps with the MTBP binding region. It has recently been shown that by binding to MDM2, RB (preferentially the hypophosphorylated form) can form a ternary complex with p53 that is distinct from the $p19^{Arf}$/MDM2/p53 complex and appears to perform a distinct function. Experiments to determine whether MTBP can compete with RB or TFIIE for binding to MDM2 are in progress. $p19^{Arf}$ binds to a region of MDM2 that lies between amino acids 154-221 (plus a further interaction point contained with the carboxy terminal 271 amino acids) and in so doing prevents MDM2 from targeting p53 for degradation.

Several MDM2 binding proteins are regulators of cell growth. Further, both of the MTBP partial homologues, BOI1 and BOI2, have been shown to have growth inhibitory activity. Therefore the effect of MTBP expression upon cell growth in culture was examined. In these experiments, it was found that, in contrast to the empty vector controls, when an expression construct for MTBP was transfected into U20S cells no colonies were produced. Since U20S cells harbor wild type p53, it was believed that the observed effect of MTBP expression may be dependent upon p53. To examine this, H1299 cells that possess a homozygous deletion of the p53 gene were transfected with MTBP and for comparison, with p53, expressed from the same vector and a vector control. Expression of MTBP was found to reduce colony formation to approximately the same degree as p53. These results indicate that MTBP possesses similar growth inhibitory properties in these p53 null cells compared to U20S cells that contained wild type p53. Similar experiments were performed with Saos-2 cells. Only a slight reduction of approximately three- to four-fold in colony formation was observed in these cells. Since, amongst other alterations, these cells lack both p53 and RB it is believed that the growth inhibitory effect of MTBP may require the presence of RB.

A possible explanation for the growth inhibitory effect observed is that MTBP acts as a general suppressor of expression, for example by "squelching" or competing for the availability of other transcription factors. To investigate this H1299 cells were transfected with a β-galactosidase expression construct and the levels of β-galactosidase were measured by western blot, in the presence of either the MTBP or p53 expression constructs and also with the pCEP vector. MTBP had no effect, whereas p53 reduces the level of β-galactosidase expression. A similar analysis was performed in a more quantitative fashion using FACs and no reduction in the number of positive cells or signal strength of CD20 when co-transfected with MTBP was observed. In contrast, a 10% reduction was seen in both with p53.

An alternative explanation for the growth inhibitory effect observed in U20S cells is the activation of p53. In these cells p53 is wild type but is transcriptionally inactive because of the presence of high levels of MDM2 (Florenes et al. J. Natl Cancer Inst. 1994 86:1297-1302). Thus, transfection of MTBP could simply compete with p53 for binding of MDM2 and in so doing release the MDM2 mediated block. To examine the possibility, levels of p53 itself and of the p53 transcriptional target, $p21^{waf1/cip1}$ in the presence of MTBP were measured. No alteration in the levels of either of these proteins was seen. Taken together, these observations indicate that high level expression of MTBP has a negative effect upon cell growth and that this is independent of p53.

Cell cycle analysis was performed to examine the possibility that MTBP might act at a specific point in the cell cycle. Cells were co-transfected with an expression construct for CD20 so that only the transfected cell population need be analyzed (van den Heuvel, S. And Harlow, E. Science 1993 262:2050-2054). At any given time in a rapidly cycling population of the cells which were used, typically 50% will have a 2N DNA complement. Initial experiments indicated that MTBP expression induces an increase in the percentage of cells with a 2N DNA complement. To examine this further and to facilitate detection of effects in this region of the cell cycle, cells were treated with the microtubule-disrupting drug nocodazole. The result of MTBP expression in U20S cells was compared to cells that were transfected with the vector alone and also with cells transfected with p53 expressed from the same vector. p53 expression induced an increase in the percentage of cells in $G_1$ from 15.9 to 24.9%. MTBP expression induced a similar effect with an increase to 24.0%. As with the growth inhibition that was detected, the possibility existed that the effect observed for MTBP expression upon the cell cycle was in some manner dependent upon p53. To examine this, a similar experiment was performed with H1299 cells. It was found that both p53 and MTBP induce a comparable increase in the percentage of cells with a 2N DNA content from 22.4 to 35.8 and 38.3%, respectively. These experiments were performed on at least three occasions and similar results were obtained each time. These results indicate that p53 is not required for MTBP mediated cell cycle arrest.

The effect of MTBP expression upon Saos-2 cells was also examined since these cells appear to be resistant to the growth inhibitory effect of MTBP expression. Analysis of these cells clearly demonstrated that expression of MTBP had no effect upon their cell cycle. These results indicate that the ability of MTBP to inhibit colony formation is consistent with its ability to alter the cell cycle. Thus, from these experiments it is believed that MTBP induces $G_1$ arrest in a p53 independent manner.

MDM2 blocks p53 mediated cell cycle arrest (Chen et al. Mol. Cell. Biol. 1996 16:2445-2452). Accordingly, its ability to inhibit the effect of MTBP was also examined. Little effect upon the level of MTBP protein was observed. However, it was found that MDM2 expression resulted in complete abrogation of the effect of MTBP in U20S cells. Thus, it is believed that MDM2 mediated inhibition of the MTBP induced cell cycle arrest does not require degradation of MTBP. Further, it is believed that MDM2 suppresses the $G_1$ arrest mediated by MTBP and since this does not require degradation of MTBP, it seems likely that the effect is a consequence of the ability of MDM2 to bind directly to MTBP.

In addition to providing nucleic acid sequences and polypeptides encoded thereby of mammalian MTBP, the present invention also relates to vectors expressing this new protein as well as host cells comprising such vector which express these new proteins. Various vectors and host cells known in the art can be used and selection of appropriate vectors and host cells for expression of MTBP can be performed routinely by those of skill in the art.

Mammalian MTBP polypeptides prepared via these vectors and host cells or synthetically are useful in raising antibodies targeted to the mammalian MTBP polypeptides. Methods for raising both polyclonal and monoclonal antibodies are well known to those of skill in the art. Thus, raising antibodies specific for the mammalian MTBP polypeptides of the present invention can be performed routinely by those skilled in the art. Such antibodies are not only useful in further elucidation of the function of this protein, but also in methods for detecting these polypeptides and in methods for identifying modulators of the expression and/or activity of this proteins.

The vectors and host cells of the present invention are also useful in the development of methods and compositions for modulating the $G_1$ phase of the cell cycle via altering expression of MTBP or levels and/or activity of MTBP. Examples of compositions capable of modulating expression of MTBP or levels or activity of MTBP include, but are not limited to antisense agents targeted to MTBP, ribozymes targeted to MTBP, peptide mimics of MTBP and modulators of MDM2 expression. Identification and development, as well as testing or screening, of such compositions can be performed routinely by those of skill in the art based upon the teachings provided herein relating to these new MTBP genes and proteins and their activity. Compositions which modulate MTBP levels or activity may be useful in suppressing tumors.

The following nonlimiting examples are provided to further illustrate the present invention.

EXAMPLES

Example 1

Cell culture, Plasmids and Antibodies

Cells were grown in RPMI supplemented with 10% fetal calf serum, and 1% penicillin, streptomycin, and neomycin (Gibco-BRL). H1299 (ATCC# CRL-5803), U20S (ATCC# HTB-96) and Saos-2 (ATCC# HTB-85) cells were obtained from the ATCC. pGAL4-DBD-MDM2 encodes full length mouse MDM2 cloned in-frame with the GAL4 DNA binding domain (DBD) of pGBT9 (Clontech). pGAL4-AD-MTBP-3' contains the carboxy terminal 380 amino acids of MTBP cloned into the XhoI site of pACT (Clontech). pBBV was generated by inserting an oligonucleotide containing the black beetle virus ribosome binding sequences from pBD7 (Dasmahapatra et al. Nucleic Acids Res. 1987 15:3933) into the HindIII and EcoRV sites of pcDNAI Neo (Invitrogen). pSK-BBV was generated by subcloning a HindIII/BglII DNA fragment containing the black beetle virus ribosome binding sequence from pBBV into the HindIII and BamHI sites of plasmid pBluescript SKII+(Stratagene). Clones identified as encoding candidate MDM2 interacting molecules in the yeast two hybrid screen analysis were amplified from pACT with GAD5 (5' gag aga gat atc gcc aat ttt aat caa agt ggg aat att 3' (SEQ ID NO:11)) and GAD3 (5' gag aga gcg gcc gct ttc agt atc tac gat tca tag atc tc 3' (SEQ ID NO:12)) primers and subcloned into the EcoRV and NotI sites of pBBV. pBBV-MTBP-3' was constructed by subcloning this PCR generated fragment from pGAL4-AD-MTBP-3' into pBBV. The PSK-MTBP construct used for in vitro translation of full length MTBP was made by sub-cloning the NotI fragment from pCEP-MTBP into the NotI site of PSK-BBV. Recombinant His$_6$-tagged MDM2 (pQE32-MDM2) was generated by cloning an EcoRV/XhoI fragment from pBBV-MDM2 encoding the full length murine MDM2 cDNA into the SmaI site of pQE32 (Qiagen). Recombinant His$_6$-tagged Δ166 (pQE31-Δ166 MDM2) contains a DNA fragment of murine MDM2 lacking the first 166 amino acid residues. The fragment was amplified from pCMVNeoBam-Mdm2 by PCR with primers MDM2 PstI (5' gag aga ctg cag gag aac aca gat gag cta cct gg 3' (SEQ ID NO:5)) and MDM2 HindIII (5' gag aga aag ct gtc agc tag ttg aag taa ctt agc a 3' (SEQ ID NO:6)) using rTth-XL polymerase (Perkin-Elmer) and cloned into the PstI and HindIII sites of pQE31 (Qiagen). MTBP (pCEP-MTBP-HA) contains full length murine cDNA for MTBP excised from the PCR-XL-TOPO vector and cloned into the NotI site of pCEP (Invitrogen). p53 contains full length human p53 cloned into the pCEP vector. The p53 antibody Ab-1 (PAb421), the MDM2 antibody used for western blotting Ab-1 (IF2) and the anti-β-galactosidase antibody Ab-1 (200-193) were purchased from Oncogene Research Products. The MDM2 antibody used for immunoprecipitation, SMP14, and the antibody used to detect p21$^{waf1/cip1}$ (F-5) were purchased from Santa Cruz Biotechnology, Inc. while the anti-Hemagglutinin A (HA) antibodies (12CA5 and 16B12) used to detect HA-tagged MTBP were purchased from Roche Molecular Biologicals and BAbCO, respectively. The anti-CD20 antibody leu16 was purchased from Becton Dickinson and the anti-mouse-IgG-FITC conjugate was obtained from Pierce.

Example 2

Yeast Two Hybrid Screen

The MATCHMAKER system (Clontech) was used to screen a mouse T-cell lymphoma library (ML4001AE) and to assess interactions between the GAL4-DBD-MTBP and GAL4-AD-MDM2 deletion mutants.

Example 3

Cloning and Analysis of MTBP

The Marathon RACE system (Clontech) was used to amplify the 5' and 3' ends of MTBP from a murine B cell CDNA. Total cellular RNA was prepared from murine SP2 (ATCC# CRL-1646) cells using RNAZOL (MBI) and poly A+RNA was isolated from this using OLIGOTEX beads (Qiagen). 5-prime RACE was performed using the gene specific oligonucleotides GSP-1 (5' tga aga ata agg ttc aac tgt acc 3' (SEQ ID NO:7)) and GSP-2 (5' cag ctt tca cgg tgt ctg ttt g 3' (SEQ ID NO:8)). PCR was performed with rTth-XL and products were cloned into pCR2.1 (Invitrogen). 3-prime RACE was also performed and confirmed the termination codon identified in the yeast two hybrid screen. Sequencing was performed using dye terminators and an ABI-373 sequencer. Homology to BO11 and BO122 was identified using the FASTA program to examine the Saccharomyces cerevisiae database at Stanford University. The full length cDNA for MTBP was prepared by PCR amplification with the oligonucleotides MTBP-5'-NotI (5' gag aga gag gcc gcg gcg cga aga gga tgg atc ggt act tgc tg 3' (SEQ ID NO:9)) and MTBP-3'-HA-NotI (5' gag aga gcg gcc gcc tac agg gag gcg taa tcg ggc aca tcg tag ggg tat ttc ttg ctc atc ttt tct acc acc 3' (SEQ ID NO:10)) using rTth-XL and the product was cloned into PCR-XL-TOPO (Invitrogen).

Example 4

In Vitro Binding and Immunoassays

For in vitro binding assays, MDM2 or Δ166-MDM2 were expressed in XL-1 bacteria (Stratagene) from the pQE32-MDM2 and pQE31-Δ166-MDM2 constructs, respectively, captured on Ni$^{++}$-agarose (Qiagen) and washed with buffers B, C and D as described by the manufacturer. Prior to all binding reactions, protein captured onto beads was run on a SDS-polyacrylamide gel and analyzed by both western blotting and staining with coomassie blue. Washed beads (100 μl) were then mixed with 10 μl of in vitro translated protein (TNT, Promega) for 3 hours at 30° C., followed by washing three times in Dignam's buffer D supplemented with 75 mM imidazole (Dignam et al. Nucleic Acids Res. 1983 11:1475-1489). Beads were then resuspended in loading buffer and analyzed by SDS-PAGE and fluorography using AMPLIFY (Amersham Pharmacia).

Cells were transfected by either the calcium phosphate-DNA co-precipitation method (Sambrook et al. 1989 Molecular Cloning, A Laboratory Manual 2nd edition Cold Spring Harbor Laboratory Press, Cold Spring Harbor, N.Y.) or by using FUGENE-6 (Roche) according to the manufacturer's instructions. For immunoprecipitation experiments cells were typically transfected with 10 μg of each plasmid and proteins were extracted 48-72 hours post transfection. Transfected cells were harvested and the cell pellet lysed in IP buffer (50 mM HEPES, pH 7.5, 150 mM NaCl, 10% glycerol, 0.1% TRITON-X100, 0.5 mg/ml BSA) in the presence of the protease inhibitors: 1-2 μg/ml aprotinin, 1-2 μg/ml leupeptin, 1 μg/ml pepstatin A, 100 μg/ml soybean trypsin inhibitor (Roche) and 1 mM phenylmethylsulfonylfluoride, for 10 minutes, on ice. The lysate was clarified by centrifugation for 10 minutes at 4° C. and the concentration of total proteins determined by Bio-Rad Protein Assay (BioRad). Between 1 and 5 mg of protein was then pre-cleared by incubation with 50 μl of protein G-sepharose (Amersham Pharmacia) for 1 hour at 4° C. Pre-cleared lysate was incubated with 1 μg of primary antibody for 1 hour at 4° C., followed by incubation with 50 μl of protein G-sepharose for 2 hours at 4° C. Immunoprecipitated complexes were washed three times with IP buffer, resuspended in 30 μl of protein sample buffer (0.1 M Tris-HCl, pH 6.8, 4% SDS, 0.2% bromophenol blue, 20% glycerol, 0.5 M DTT) and subjected to SDS-PAGE followed by transfer to Hybond-ECL membrane (Amersham Pharmacia). Following incubation with primary antibodies and subsequently with anti-mouse-IgG-HRP (Amersham Pharmacia), the signal was detected by enhanced chemiluminescence with RENAISSANCE (NEN).

Example 5

FACS, Cell Cycle Analysis and Colony Assays

Saos-2 and U20S cells were transfected using FUGENE-6 with the indicated plasmids. Cells were harvested and analyzed by FACS essentially as described by Chen et al. Mol.

Cell Biol. 1996 16:2445-2452. Briefly, nocodazole was added to the indicated cells at 50 ng/ml for 12 hours prior to harvesting. Cells were harvested 48-72 hours after the addition of FUGENE-DNA complexes and washed in Dulbecco's phosphate buffered saline containing 1% bovine serum albumin (PB). CD20 positive cells were detected using anti-CD20 antibody and an anti-mouse-IgG-FITC conjugate. Cells were fixed in ethanol and then stained in propidium iodide. Cells were analyzed using a FACSCAN (Becton Dickinson) and LYSIS-II software. H1299 cells were transfected using either the calcium phosphate precipitation method or FUGENE-6. Typically for the calcium phosphate precipitate procedure, 24 hours after removal of precipitates, hygromycin B (Roche) was added to a final concentration of 200 μg/ml. Cells were maintained under selective conditions for 72 hours, washed and refed with hygromycin-free complete media. Nocodazole (Sigma) was added as indicated at a concentration of 20 ng/ml, 16 hours before cells were harvested for analysis.

For colony formation assays, cells were transfected with the indicated plasmids and 24-48 hours after addition of DNA, hygromycin-B was added at a final concentration of 200 μg/ml. Cells were refed every three days with media containing Hygromycin-B until colonies were visible. For some experiments cells were stained with Giemsa.

What is claimed is:

1. An isolated polypeptide comprising an amino acid sequence of a mammalian MDM2 binding protein selected from the group consisting of SEQ ID NO:2 and SEQ ID NO:4, capable of binding to a mammalian MDM2 polypeptide and thereby inducing arrest of the cell cycle.

2. The isolated polypeptide of claim 1 consisting of the amino acid sequence set forth in SEQ ID NO:2 or SEQ ID NO:4.

* * * * *

UNITED STATES PATENT AND TRADEMARK OFFICE
CERTIFICATE OF CORRECTION

PATENT NO. : 7,304,142 B2  Page 1 of 1
APPLICATION NO. : 11/650159
DATED : December 4, 2007
INVENTOR(S) : Boyd et al.

It is certified that error appears in the above-identified patent and that said Letters Patent is hereby corrected as shown below:

At column 1, line 13, please delete:

"This invention was supported in part by funds from the U.S. government (NIH Grant No. CA70165) and the U.S. government may therefore have certain rights in the invention."

and insert:

--This invention was made with government support under Grant No. CA70165 awarded by the National Institutes of Health. The U.S. government has certain rights in the invention.--.

Signed and Sealed this

Fifteenth Day of June, 2010

David J. Kappos
*Director of the United States Patent and Trademark Office*